(12) United States Patent
von Schenck et al.

(10) Patent No.: US 12,257,205 B2
(45) Date of Patent: Mar. 25, 2025

(54) PREVENTING INFECTIONS IN NON-STERILE AIR-CIRCULATING MEDICAL DEVICES

(71) Applicant: Physio-Control, Inc., Redmond, WA (US)

(72) Inventors: Erik von Schenck, Lomma (SE); Cathlene Buchanan, Shoreline, WA (US); Neal Clark, Snohomish, WA (US); Tyson Taylor, Bothell, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 938 days.

(21) Appl. No.: 17/357,259

(22) Filed: Jun. 24, 2021

(65) Prior Publication Data

US 2021/0401666 A1 Dec. 30, 2021

Related U.S. Application Data

(60) Provisional application No. 63/044,821, filed on Jun. 26, 2020.

(51) Int. Cl.
*A61H 31/00* (2006.01)
*A61L 9/12* (2006.01)
(Continued)

(52) U.S. Cl.
CPC ............ *A61H 31/006* (2013.01); *A61L 9/122* (2013.01); *A61L 9/20* (2013.01); *H05K 7/20145* (2013.01);
(Continued)

(58) Field of Classification Search
CPC ......... A61H 31/00; A61H 31/006; A61L 9/00; A61L 9/12; A61L 9/18; A61L 9/20;
(Continued)

(56) References Cited

U.S. PATENT DOCUMENTS

| 5,422,787 A | * | 6/1995 | Gourdine | ........... H05K 7/20154 361/695 |
| 6,876,548 B2 | * | 4/2005 | Yatougo | ............. H05K 7/20145 361/692 |

(Continued)

FOREIGN PATENT DOCUMENTS

| CN | 110812182 A | * | 2/2020 | ............. A61H 31/00 |
| CN | 210020259 U | * | 2/2020 | |
| CN | 110912182 A | * | 3/2020 | .............. H02J 3/381 |

*Primary Examiner* — Brandy S Lee
*Assistant Examiner* — Mishal Zahra Hussain
(74) *Attorney, Agent, or Firm* — Miller Nash LLP

(57) ABSTRACT

The present disclosure includes various examples for cooling electronics within a medical device while preventing or reducing the risk of an interior of the medical device being contaminated with a pathogen. The present disclosure includes a medical device having an air deflector to deflect potentially contaminated air from infecting a patient or caregiver. The present disclosure also includes medical devices with disinfectant devices installed to disinfect air either before entering the medical device or before exiting the device. Other examples of the present disclosure include medical devices that are sealed from outside air and fluids, and which may include a cooling device on an exterior surface which may be cleaned and/or removed after each use.

9 Claims, 8 Drawing Sheets

(51) Int. Cl.
*A61L 9/20* (2006.01)
*H05K 7/20* (2006.01)

(52) U.S. Cl.
CPC ..... *H05K 7/20181* (2013.01); *A61H 2201/01* (2013.01); *A61H 2201/50* (2013.01); *A61L 2202/24* (2013.01)

(58) Field of Classification Search
CPC ......... A61L 2202/24; A61L 2/26; H05K 7/20; H05K 7/20145; H05K 7/00; A61N 1/39
USPC .................. 361/679.46, 692, 694, 695, 831; 165/104.33, 249; 601/41
See application file for complete search history.

(56) References Cited

U.S. PATENT DOCUMENTS

| | | | |
|---|---|---|---|
| 9,320,678 B2 * | 4/2016 | Illindala | A61H 31/006 |
| 9,398,998 B2 * | 7/2016 | Jensen | A61H 31/00 |
| 10,682,773 B2 * | 6/2020 | Wagner | H05K 7/20918 |
| 2013/0128450 A1 * | 5/2013 | Redshaw | G06F 1/20 |
| | | | 73/861.47 |
| 2019/0298606 A1 * | 10/2019 | Reynolds | A61H 31/007 |

* cited by examiner

PREVENTING INFECTIONS IN NON-STERILE AIR-CIRCULATING MEDICAL DEVICES

PRIORITY

This disclosure claims benefit of U.S. Provisional Application No. 63/044,821, titled "PREVENTING INFECTIONS IN NON-STERILE AIR-CIRCULATING MEDICAL DEVICES," filed on Jun. 26, 2020, which is incorporated herein by reference in its entirety.

FIELD

The present disclosure relates to devices and method for preventing infections in non-sterile air-circulating medical devices, such as Cardiopulmonary Resuscitation (CPR) devices, defibrillators, and other medical devices which may circulate air, such as to cool electronics within the medical device.

BACKGROUND

Medical devices today, such as, but not limited to, mechanical CPR devices, defibrillators, and monitors, require an increasing amount of processing power. Conventional medical device circulate air within the interior of the device, such as by an air channel, which may or may not include a fan, to cool the electronics within the device during operation.

The air used to circulate in the medical devices is pulled from the surrounding environment and can contain viruses, bacteria, or other pathogens from infected patients or others around the patient. The air circulation system in conventional medical devices may then pass those pathogens to another patient or medical personnel.

SUMMARY

In some examples, the present disclosure includes a mechanical CPR device, having a central unit having an internal chamber with one or more electronic components, a fan configured to intake air to the internal chamber, and an exhaust configured to eject air from the internal chamber. An air deflector is attached, either permanently or removably to a body of the CPR device to direct air toward a lower body of a patient and prevent the intake air from mixing with the exhaust air, the air deflector including an air intake path and an exhaust path.

In some examples, the present disclosure includes a CPR device, similar to the CPR device discussed above. However, alternatively or additionally to the air deflector device being attached, the CPR device can have a hose connected to the exhaust to guide the air ejected from the internal chamber away from the mechanical CPR device.

In some examples, the present disclosure includes a CPR device, similar to the CPR devices, discussed above. However, alternatively or additionally to the air deflector device or hoses, the CPR device may include a filter disposed in the internal chamber, the filter configured to filter the air prior to entering the internal chamber or exiting the internal chamber through the exhaust.

In some examples, the present disclosure includes a CPR device, similar to the CPR devices. However, alternatively or additionally to the examples discussed above, the CPR device may include a disinfectant device to disinfect an internal chamber of the central unit. The disinfectant device may be an ultraviolet lamp or an infrared radiator, for example.

In other examples, the present disclosure includes a medical device having an internal chamber having one or more electrical components, an air intake configured to intake air to the internal chamber, a fan configured to guide air to the air intake, an exhaust configured to eject air from the internal chamber, and a hose connected to the exhaust to guide the air ejected from the internal chamber away from the medical device.

In other examples, the present disclosure includes a medical device, comprising an internal chamber having one or more electrical components connected to a hot plate, and a heat exchanger attached to the internal chamber opposed to the hot plate. The heat exchanger can include a fin stack adjacent to the internal chamber; a fluid channel to guide fluid through the fin stack; and a fan to direct fluid into the fluid channel. The heat exchanger may be permanently or removably attached to the medical device.

In another example, the present disclosure includes a mechanical CPR device, having a hood having an internal chamber configured to house one or more electronic components, a back plate, a first leg having a first end coupled to the back plate and a second end connected to the hood, a second leg having a first end coupled to the back plate and a second end connected to the hood, and a cooling conduit coupled to the first leg and the internal chamber, the cooling conduit configured to lower the temperature of the one or more electronic components.

These and other features and improvements of the present application and the resultant patent will become apparent to one of ordinary skill in the art upon review of the following detailed description when taken in conjunction with the several drawings and the appended claims.

DETAILED DESCRIPTION

As disclosed herein, examples are directed preventing infections in non-sterile air-circulating medical devices. Examples are directed to different configurations that may be used to either prevent or reduce a risk of a device from being contaminated with pathogens during operation.

Figure 1:
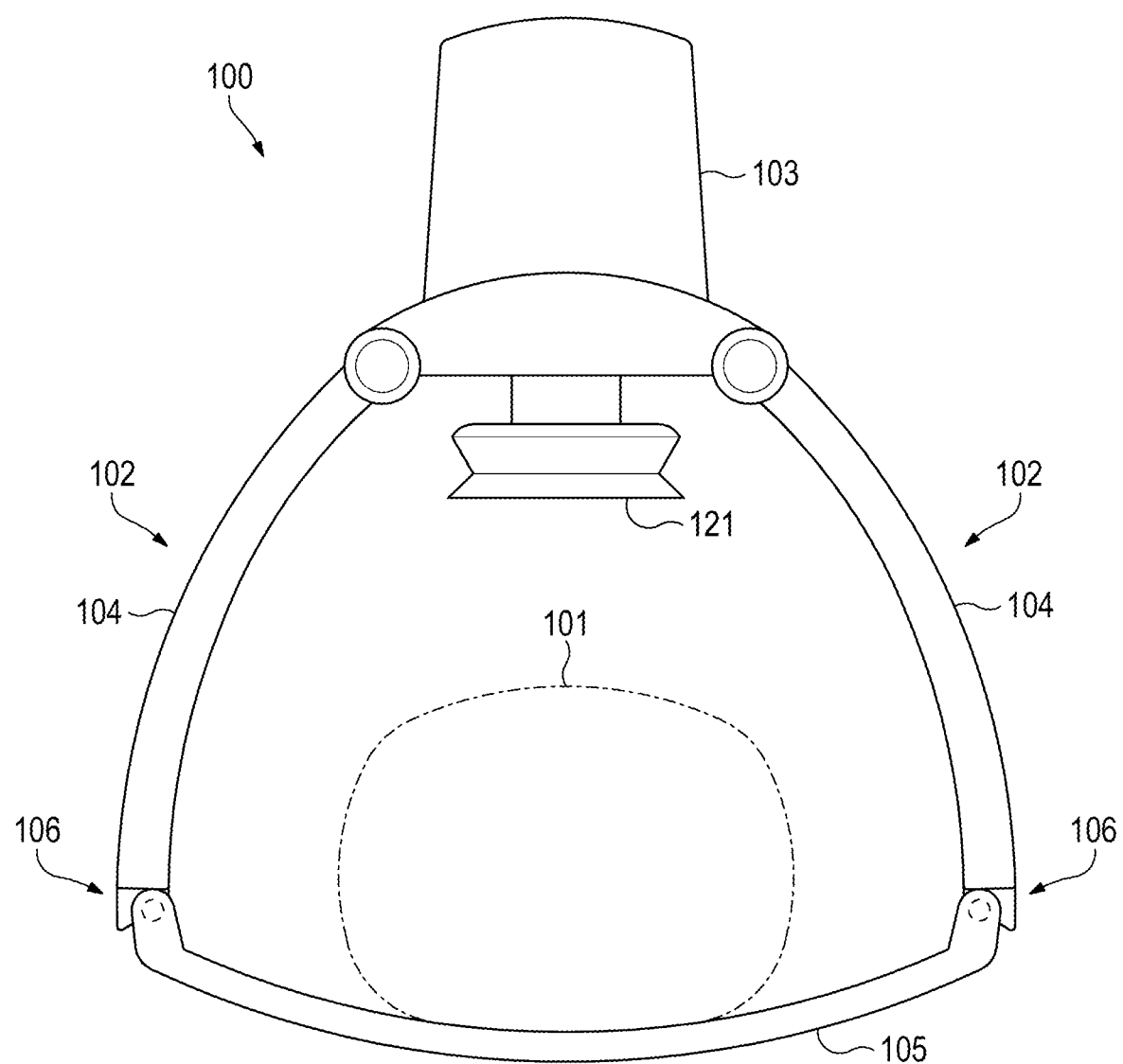
FIG. 1 is an exemplary CPR device that circulates air within an interior of the CPR device.

FIG. 1 is a front view of the CPR device 100 of FIG. 1, also showing a representation of a patient 101 within the CPR device 100. As will be understood by one skilled in the art, the mechanical CPR device 100 may include additional components not shown in FIG. 1. As illustrated in FIG. 1, a CPR device 100 may include a support structure 102 and a central unit 103, which may also be referred to herein as a hood. The support structure 102 may include a support leg 104 and a base member 105. The support leg 104 and the base member 105 meet at a junction 106 between the support leg 104 and the base member 105.

The central unit 103 may be configured to deliver CPR chest compressions to the patient 101. The central 103 may include, for example, a motor-driven piston 121 configured to contact the patient's chest to provide the CPR chest compressions. Examples of the disclosure, however, are not limited to a motor-driven piston 121, and a compression mechanism may include compression arms, such as one or more rigid or semi-rigid arms and/or a compression element and belt combination. The central unit 103 may also include a number of electronic components to drive the motor-driven piston 121 or any other type of chest compression mechanism used.

The base member, or back plate, 105 may be configured to be placed underneath the patient 101, for example when the patient 101 is lying on the patient's back.

The support leg 104 may be configured to support central unit 103 at a distance from the base member 105. For example, if the base member 105 is underneath the patient 101, who is lying on the patient's back, then the support leg 104 may support the central unit 103 at a sufficient distance over the base member 105 to allow the patient 101 to lay within a space between the base member 105 and the central unit 103, while positioning the central unit 103 over the patient's chest.

Figure 2:
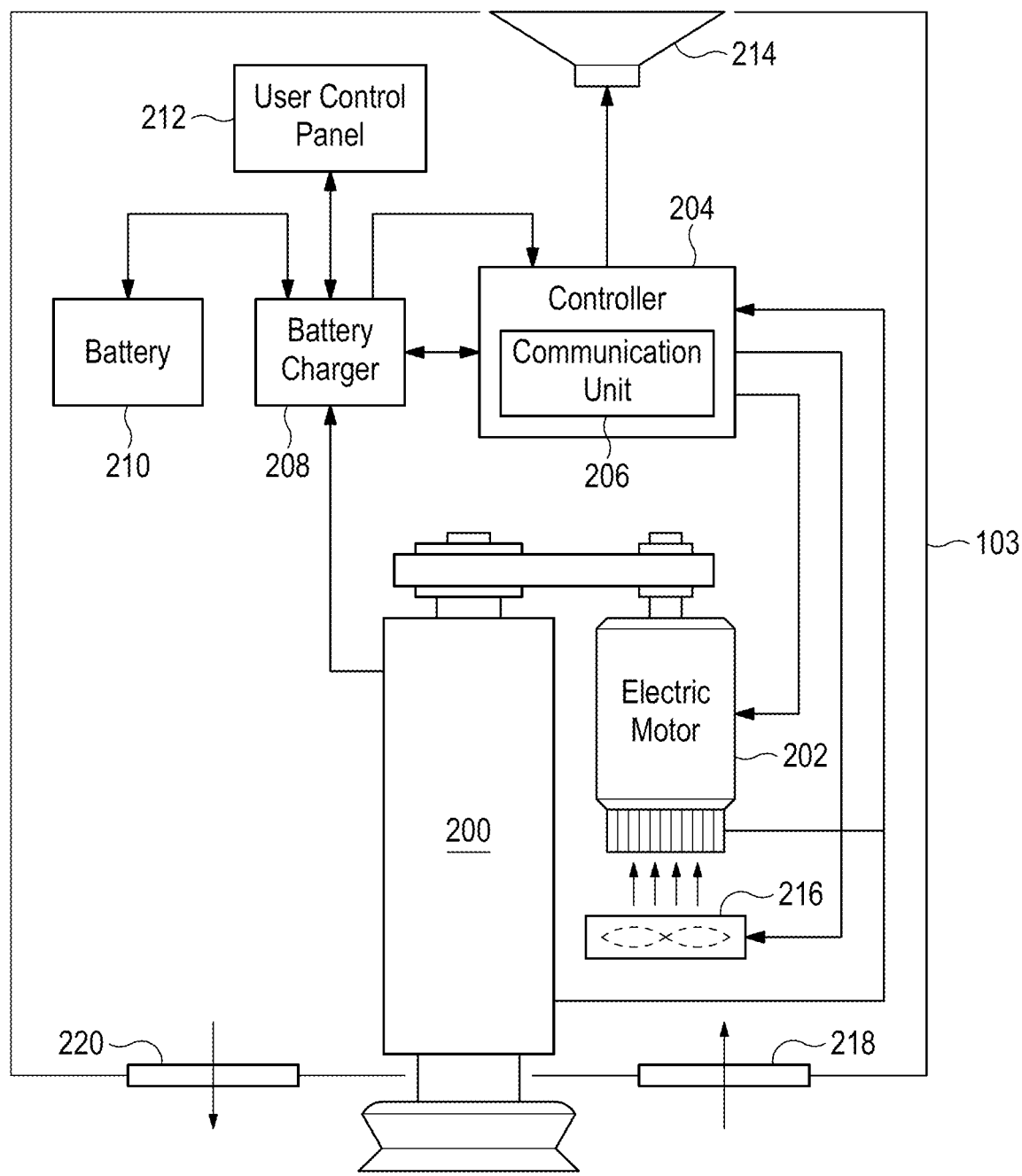
FIG. 2 is a block diagram of an example central unit of the CPR device of FIG. 1.

FIG. 2 illustrates a block diagram of the central unit 103. The central unit 103 may include, a number of different components, such as a chest compression mechanism 200, an electric motor 202, a controller 204, a communication unit 206, a battery charger 208, a battery 210, a user control panel 212, a speaker 214, and a fan 216. As will be understood by one skilled in the art, many other types of components may also be included in the central unit 103.

The controller 204 may be in electrical communication with the chest compression mechanism 200. The chest compression mechanism 200 may include a driver configured to drive the compression mechanism 200 to cause the compression mechanism 200 to perform compressions to a chest of patient. The controller 204 provides instructions to the chest compression mechanism 200 to operate the chest compression mechanism 200 at a number of different rates, depths, heights, and duty cycles.

The controller 204 may include a processor, which may be implemented as any processing circuitry, such as, but not limited to, a microprocessor, an application specific integration circuit (ASIC), programmable logic circuits, etc. The controller 204 may further include a memory coupled with the processor. Memory can include a non-transitory storage medium that includes programs configured to be read by the processor and be executed upon reading. The processor is configured to execute instructions from memory and may perform any methods and/or associated operations indicated by such instructions. Memory may be implemented as processor cache, random access memory (RAM), read only memory (ROM), solid state memory, hard disk drive(s), and/or any other memory type. Memory acts as a medium for storing data, such as event data, patient data, etc., computer program products, and other instructions.

Controller 204 may further include a communication module 128. Communication module 128 may transmit data to a post-processing module 130. Alternately, data may also be transferred via removable storage such as a flash drive. While in module 130, data can be used in post-event analysis. Such analysis may reveal how the CPR machine was used, whether it was used properly, and to find ways to improve future sessions, etc.

Communication unit 206 may further communicate with other devices. Communication between communication unit 206 and other device could be direct, or relayed through a tablet or a monitor-defibrillator.

The controller 204 may be located separately from the chest compression mechanism 200 and may communicate with the chest compression mechanism 200 through a wired or wireless connection 134. The controller 204 also electrically communicates with a user control panel 212. As will be understood by one skilled in the art, the controller 204 may also be in electronic communication with a variety of other devices, such as, but not limited to, another communication device, another medical device, etc.

The chest compression mechanism 200 may include one or more sensors configured to transmit information to controller 204. For example, chest compression mechanism 200 can include a physiological parameter sensor for sensing a physiological parameter of a patient and to output a physiological parameter sensor signal that is indicative of a dynamic value of the parameter. The physiological parameter can be an Arterial Systolic Blood Pressure (ABSP), a blood oxygen saturation (SpO2), a ventilation measured as End-Tidal CO2 (ETCO2), a temperature, a detected pulse, etc. In addition, this parameter can be what is detected by defibrillator electrodes that may be attached to patient, such as ECG and impedance.

Operations of the mechanical CPR device 100 may be effectuated through the user control panel 212. The user control panel 212 may be external to or integrated with a display. For example, in some examples, the user control panel 212 may include physical buttons located on the CPR device 100, while in other examples, the user control panel 212 may be a touch-sensitive feature of a display. The user control panel 212 may be located on the mechanical CPR device 100, or may be located on a remote device, such as a smartphone, tablet, PDA, and the like, and is also in electronic communication with the controller 204.

During a CPR session of compressions, controller 204 can generate or receive an instruction (either pre-programmed or customized based on any parameters or other data) to drive the compression mechanism 200 to administer a chest compression. All of the electrical components of the CPR device 100 can generate heat as they CPR device 100 operates. To reduce the internal temperature of the central unit 103, the central unit 103 can also include an air intake 218 and an exhaust 220. The fan 216 turns on when an internal temperature of the central unit 103 reaches a first pre-determined temperature, such as, but not limited to, 40 degrees Celsius and can stop when the internal temperature is below a second pre-determined temperature, such as, but not limited to, 30 degrees Celsius. The fan 216 can pull air in from the atmosphere through the air intake 218. The air can circulate through the central unit 103 and can exit the central unit 103 through the exhaust 220.

As mentioned above, however, this air may be contaminated and may contain pathogens. As the air exits through the exhaust 220, the infected air may be dispersed into the atmosphere and infect people surrounding the CPR device, such as a caregiver. While CPR device 100 is illustrated in FIGS. 1 and 2, examples of the disclosure are not limited to this particular CPR device and may be used with any CPR device that includes an air intake 218 and an exhaust 220 for cooling electronics.

Figure 3:
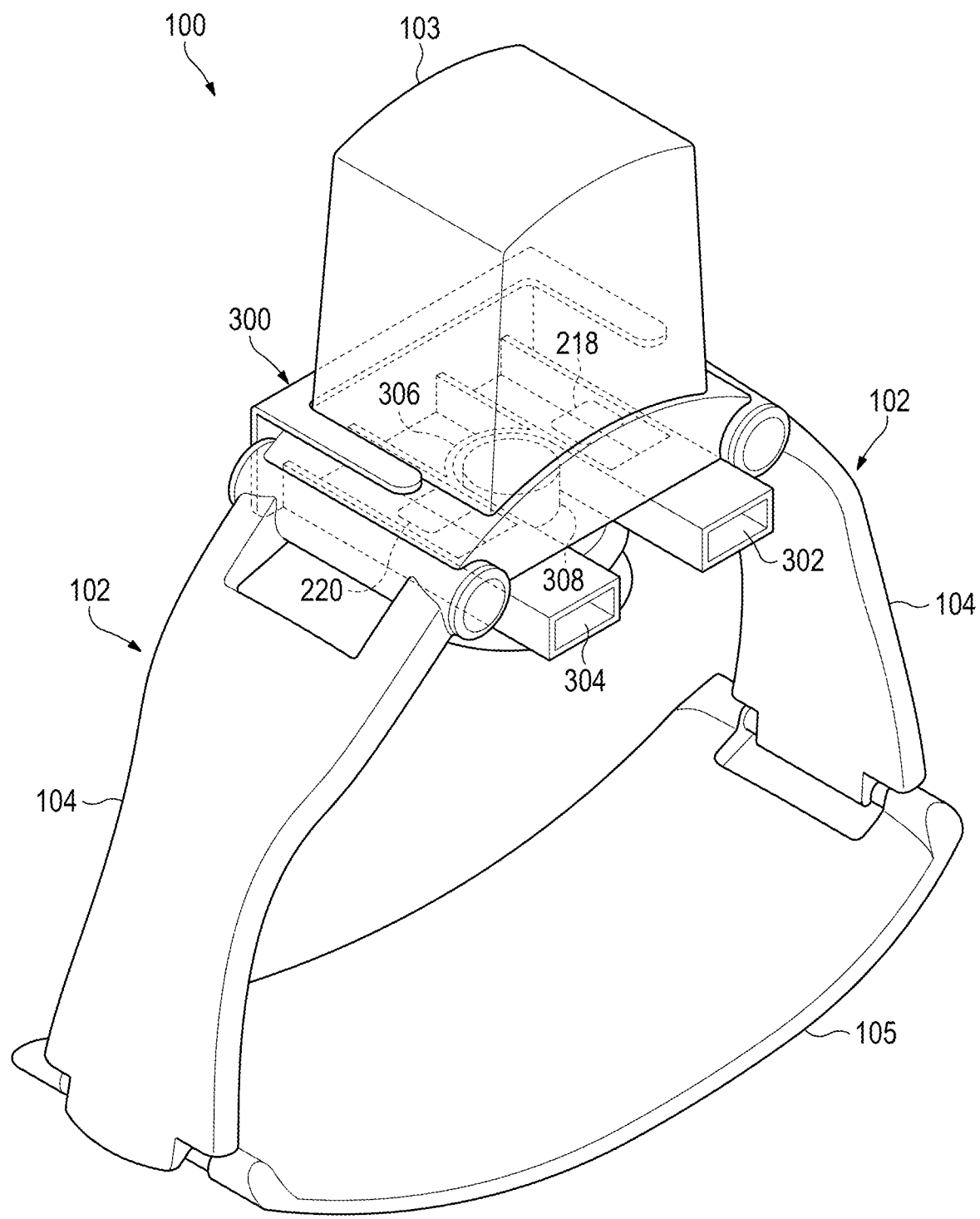
FIG. 3 is an exemplary CPR device with an attached air deflection device according to some examples of the disclosure.
Figure 4:
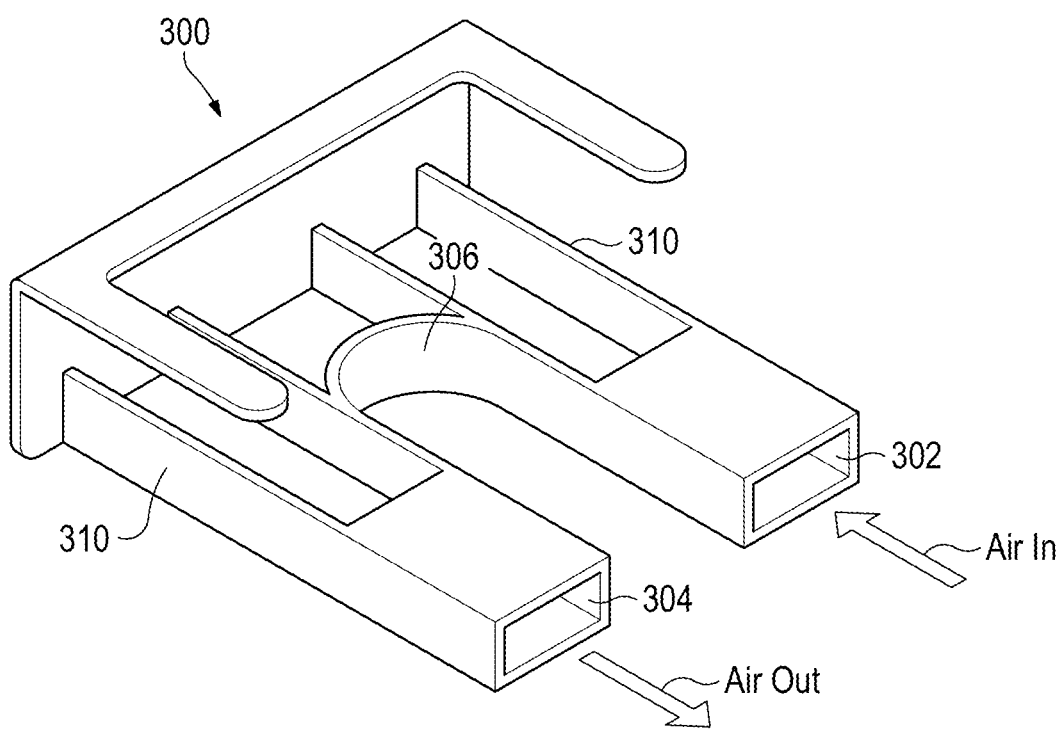
FIG. 4 is a perspective view of the air deflection device of FIG. 3.

In some examples, as illustrated in FIGS. 3 and 4, an air deflector device 300 may be included with the CPR device 100. The air deflector device 300 can attach to the support structure 102. As illustrated in FIG. 3, the air deflector device can have a "C" shape and may attach to one side of the CPR device 100 along the support structure 102. The air deflector device 300 can block air from the attached side of the support structure from entering the air intake 218. While a "C" shape air deflector device 300 is shown in FIG. 3, the air deflector device 300 can be any shape that can attached to a support structure 102 of the CPR device 100.

The air deflector device 300 can have an air intake path 302 and an exhaust path 304. The air intake path 302 and the exhaust path 304 can define an opening 306 which can accommodate a plunger 308 of the chest compression mechanism 200. The opening 306 can allow the plunger to operate without interference from the air deflector device. The edges 310 of the air deflector device 300 may protrude upwards, such as perpendicular from a surface, to prevent air in the air intake path 302 from mixing with the air in the exhaust path 304.

The air deflector device 300 can attach to the support mechanism to direct air from the air intake path 302 and the exhaust path 304 away from a head of a patient. That is, the air intake path 302 and the exhaust path 304 are directed toward the feet of a patient. In some examples, the air deflector device 300 may also be angled or otherwise tilted in a downward direction.

The air deflector device 300 can prevent or reduce potentially contaminated air from a patient from entering the central unit 103 through the air intake 218.

The air deflector device 300 may be permanently attached and integrated with the CPR device 100 in some examples. In other examples, the air deflector device 300 may be removable from the CPR device 100 and either be cleaned or disposed after use.

In some examples, rather than an air deflector device, the CPR device 100 may attach to one or more hoses, tubing, or other conduit to receive air and/or exhaust air in or from the central unit 103 away from a rescue scene. For example, in some examples, as illustrate in FIG. 5, a hose 500 may be connected to the air intake 218 and/or the exhaust 220. The hose 500 may connect to the air intake 218 and/or the exhaust 220 using any known connection means, such as any known tube or pipe fitting, threaded means, etc.

Figure 5:
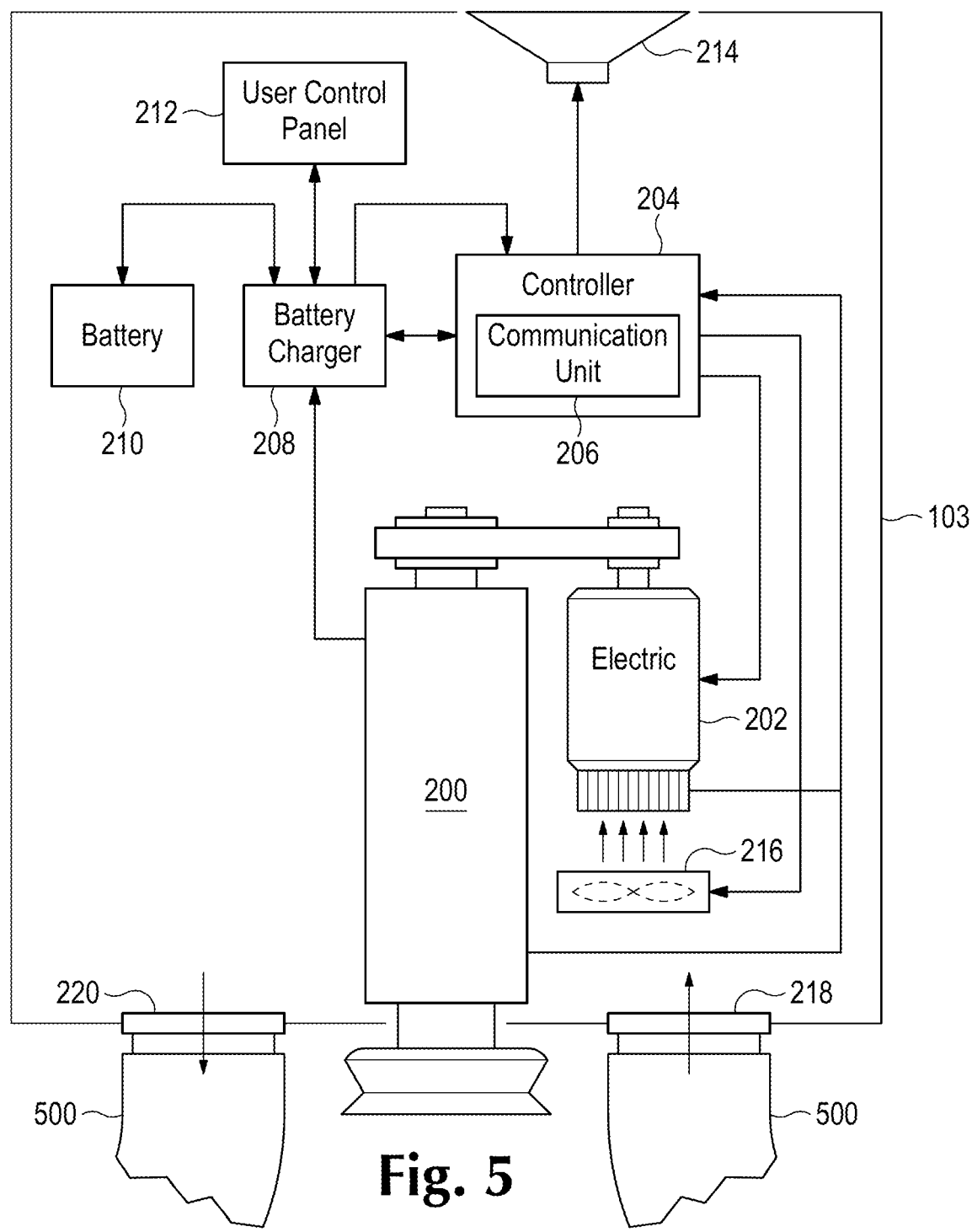
FIG. 5 is a block diagram of another example central unit of the CPR device of FIG. 1 according to some examples of the disclosure.

While FIG. 5 illustrates a hose 500 connected to both the air intake 218 and the exhaust 220, examples of the disclosure are not limited to this configuration. The hose 500 may be connected to only one of the air intake 218 or the exhaust 220 in some configurations.

For example, the CPR device 100 may be used in an ambulance while transporting a patient. A hose 500 may be connected to the exhaust 220 and be placed outside a window of the ambulance, so air exhausted from the CPR device 100 is exhausted outside the ambulance. Alternatively or additionally, a hose 500 may be connected to the air intake 218 and the opposite end out a window, such as a window opposite the hose 500 if connected to the exhaust 220. Then air from outside the ambulance may be used to cool the electronics in the central unit 103 and may be exhausted either outside the ambulance or within the ambulance itself.

Since the air is directed into the central unit 103 from outside the ambulance, then any pathogens within the air of the ambulance are not drawn into the central unit 103. The use of the CPR device 100 with one or more hoses 500 attached is not limited to an ambulance environment. Such an example may also be implemented in a medical facility and the hoses 500 may either be connected to a venting system or clean air system in the facility to either eject air to or receive air from.

Figure 6:
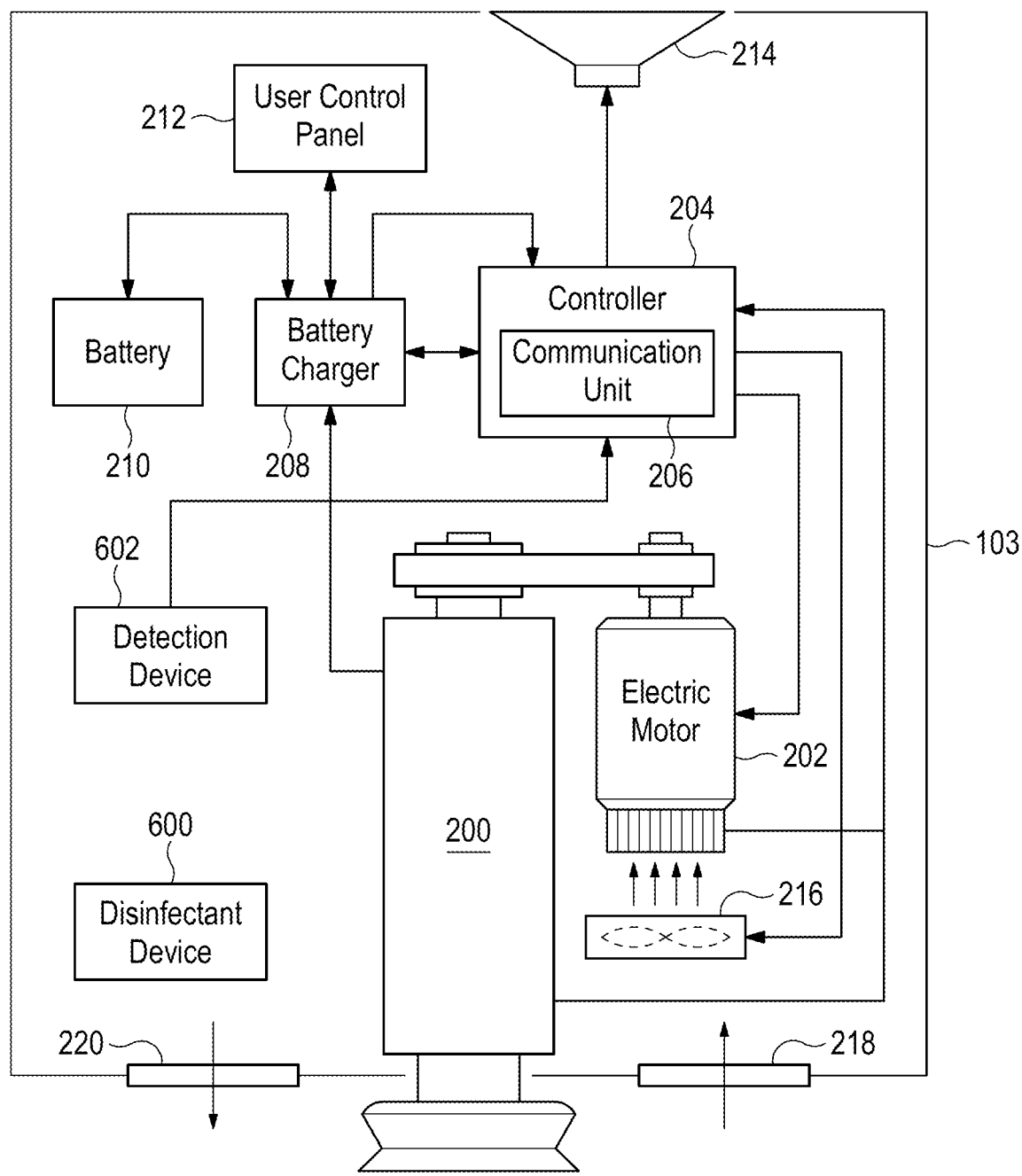
FIG. 6 is a block diagram of another example central unit of the CPR device of FIG. 1 according to some examples of the disclosure.

Additionally or alternatively to the examples discussed above with respect to FIGS. 1-5, in some examples, the interior of the central unit 103 may include one or more disinfectant devices 600. The disinfectant device 600 may be included anywhere within the central unit 103, but for ease of discussion and illustration, is shown in FIG. 6 to be located near the exhaust 220. The disinfectant device 600, however, may be placed anywhere in the air flow path of the central unit 103, including near the fan 216 or the air intake 218. That is, the disinfectant device 600 may disinfect the air prior to entering the airflow path of the central unit 103 through the air intake 218, prior to exiting the central unit 103 through the exhaust 220, and/or anywhere else in the air flow path of the central unit 103.

The disinfectant device 600 may be any device that can disinfect and/or filter the air to remove pathogens. For example, in some configurations, the disinfectant device 600 may be a high-efficiency particulate air (HEPA) filter. This filter may filter out pathogens in the air path so they are not sent out into the atmosphere around the CPR device 100.

The disinfectant device 600 may be an ultra-violet (UV) light or infrared (IR) radiator that can disinfect the interior of the central unit 103, as well as the air within the central unit 103, in some configurations. In some configurations, multiple disinfectant devices 600 of different or same types may be provided in the central unit 103.

In some configuration, an interior or airflow path of the central unit 103 may be lined with an antibacterial surface, such as silver, copper, etc. This may be in addition or alternative to the various examples provided above. In other configurations, the entire central unit 103 may be released from the support legs 104 and replaced with a new, clean central unit 103 after each use. The old central unit 103 may be stored for an extended period of time to disinfect or may be cleaned with disinfectant.

Additionally or alternatively to the examples discussed above, the central unit 103 may also include a detection device 602, such as an optical sensing device, which may monitor either the intake and/or exhaust air quality. The detection device 602 can be coupled to the controller 204. If the detection device 602 detects that the intake and/or exhaust air quality does not predetermined requirements, then the detection device 602 can output a signal to the controller 204 which can further generate a signal to alert the caregiver that the central unit 103 has been contaminated, either through the speaker 214 or a connected display device.

Examples of the disclosure are not limited to a CPR device, as shown in FIG. 1. As will be understood by one skilled in the art, the examples discussed above may be implemented in any medical device which circulates air. Other medical devices can be a defibrillator, a monitor, a monitor-defibrillator, a ventilator, a capnography device, or any other medical device. Each of these medical devices may have electronic devices that require cooling. Any of the examples discussed above may be included in or with the medical device to prevent a caregiver or patient from potentially inhaling or otherwise being exposed to contaminated air or fluids.

Figure 7:
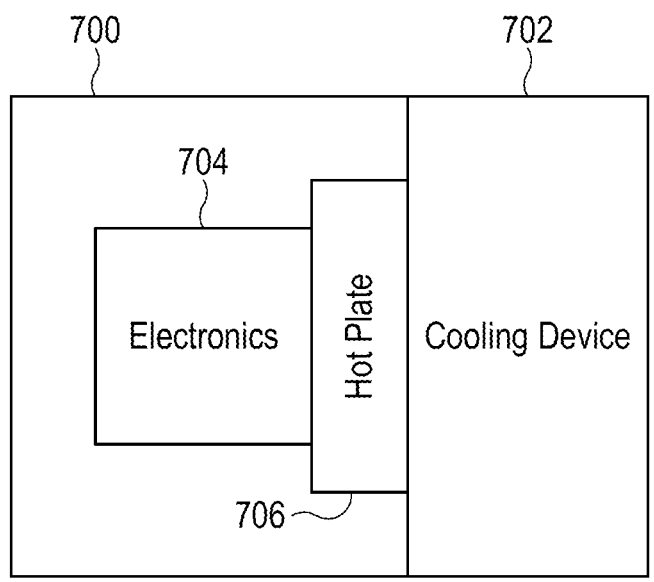
FIG. 7 is a block diagram of a medical device with a cooling device attached according to some examples of the disclosure.

In some examples, a cleanable and/or removable cooling system may be provided to prevent contaminated fluids from entering a medical device. FIG. 7 is a block diagram of a medical device 700 which includes a cooling device 702, which may be removable in some configurations. As will be understood by one skilled in the art, the medical device 700 may include additional components not shown in FIG. 7, such as various ports, displays, user inputs, etc. The medical device 700 can be any medical device that has electronic components, such as, but not limited to, a CPR device, a defibrillator, a monitor, a monitor-defibrillator, a ventilator, a capnography device, or any other medical device.

The medical device 700 includes an interior having one or more electronic components 704 which are coupled to a hot plate 706. The hot plate 706 can then abut or connect to a cooling device 702 which is separated and sealed off from the interior of the medical device 700 including the one or more electrical components. During operation of the medical device 700, as the one or more electrical components become heated, the heat may transfer to hot plate 706, which can then be cooled by the cooling device 702. The interior of the medical device 700 can be sealed from the cooling device 702.

After use, the cooling device 702 can be cleaned to remove any pathogens and/or removed and replaced with a new cooling device 702 for the next use. In such an example, the interior of the medical device 700 housing the electrical components is not contaminated during use of the medical device 700, since the interior is sealed from any sort of pathogens.

Figure 8:
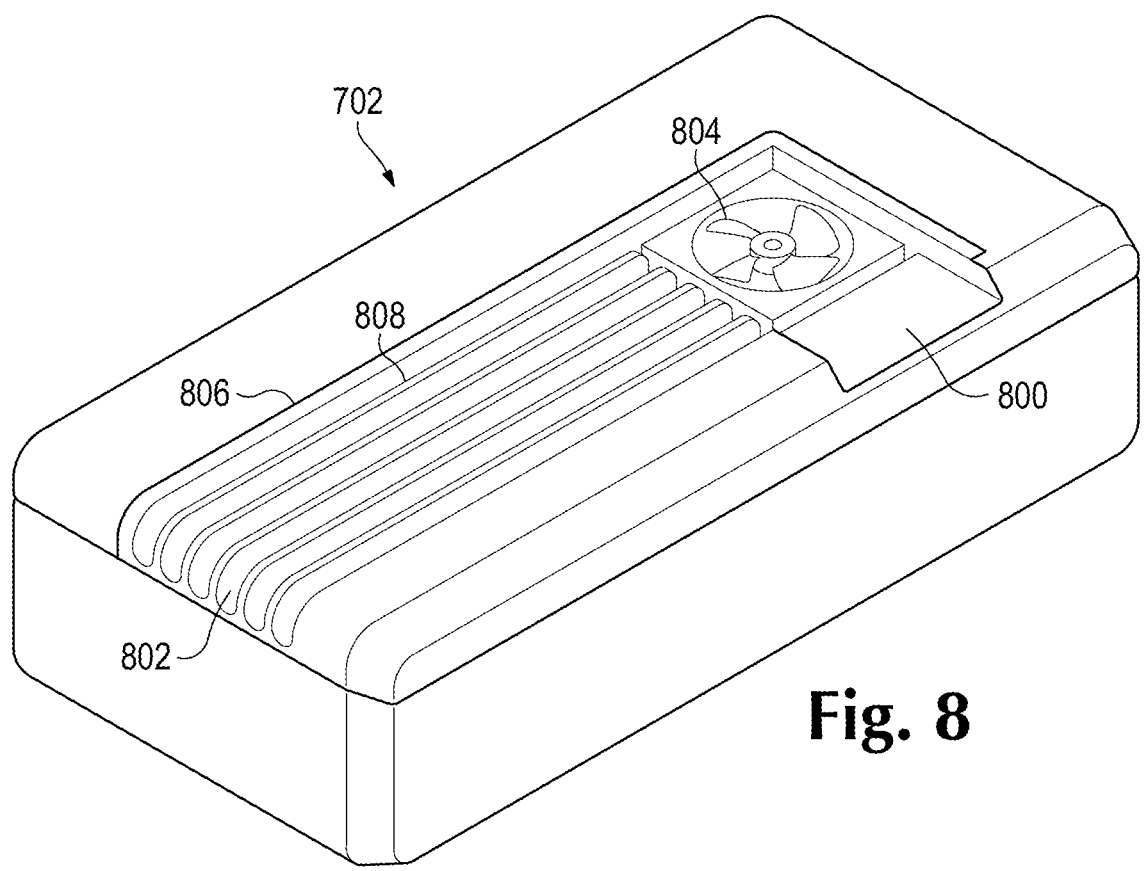
FIG. 8 is a perspective view of an example cooling device of FIG. 7 according to some examples of the disclosure.

FIG. 8 illustrates an example of a cooling device 702 which may be included with or otherwise attached to a medical device 700. The cooling device may snap on or attach in other ways, such as by screws, to the medical device 700 so that the cooling device 702 abuts the hot plate 706.

The cooling device 702 include an air flow path that has an air intake 800 and an exhaust 802. The air flow path may also include a fan 804 that can begin to circulate air once an internal temperature of the interior of the medical device 700 reaches a first predetermined temperature. The fan 804 may turn off when the internal temperature of the interior of the medical device 700 is below a second predetermined temperature, similar to the fan 216 discussed above. The air flow path may also include a heat sink 806 which can transfer heat from the hot plate 706 to a fluid medium, which in the example shown in FIG. 8 would be air, where the heat is dissipated away from the medical device 700. The heat sink 806 may include a number of fins 808, which are plates which extend perpendicular to a face of the cooling device 700. Air or other fluid can flow through the fins 808 to transfer the heat from the one or more electrical components away from the medical device 700.

The fan 804 included in the cooling device 702 may be a waterproof fan that can be cleaned with a solution to remove any potential pathogens. In some examples, the cooling device 702 may also include a disinfectant device 600, discussed above. The disinfectant device 600 may disinfect any air or fluid that either enters or exits the air flow path to prevent any potential pathogens from being distributed in the atmosphere surrounding the medical device 700.

Additionally or alternatively, the air flow path of the medical device 700 may be coated with an antibacterial coating, such as, but not limited to, silver or copper.

Figure 9:
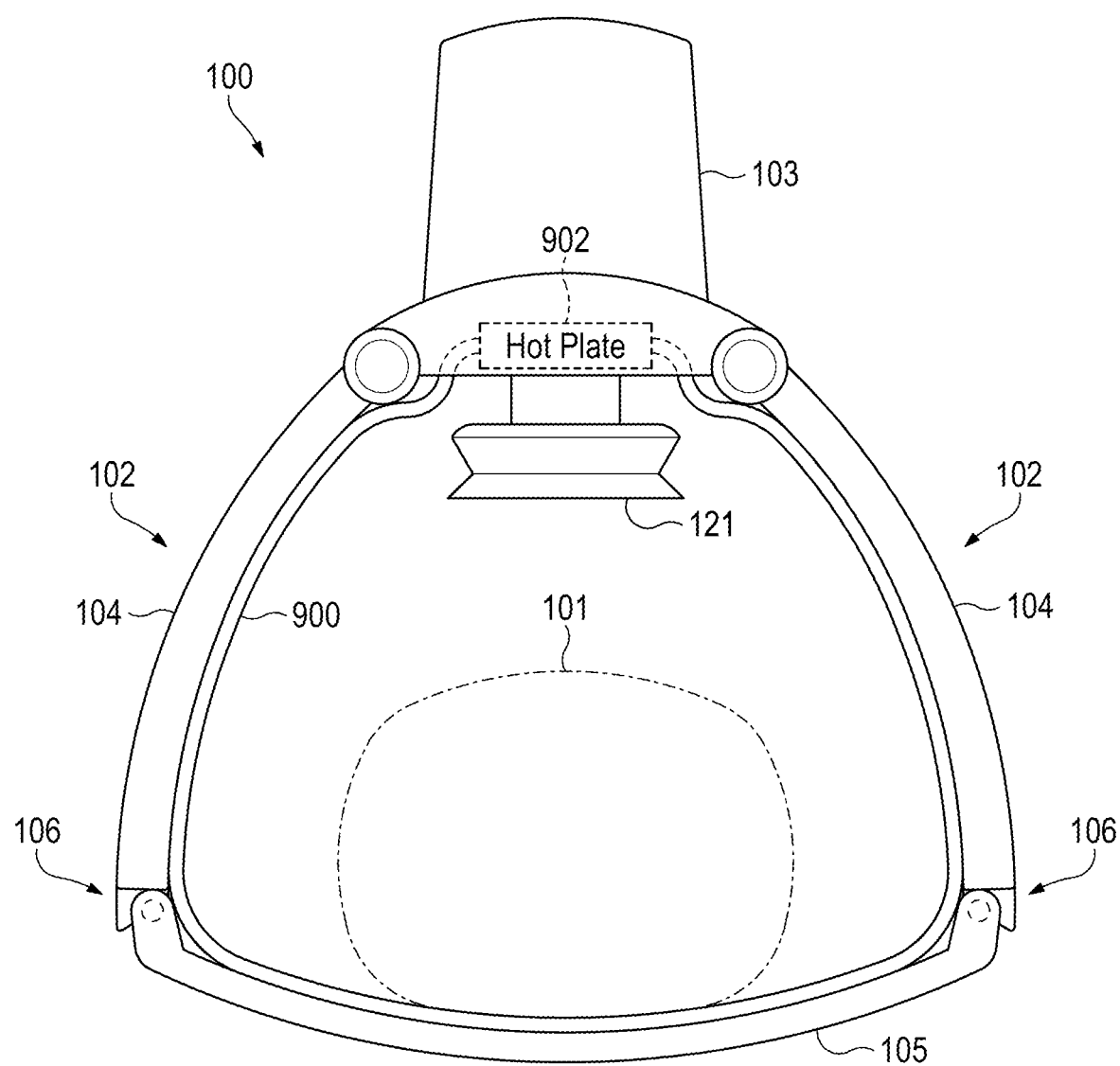
FIG. 9 is another exemplary CPR device according to some examples of the disclosure.

In some examples, a fluid may be used as a cooling device attached to a medical device. For example, FIG. 9 illustrates a CPR device 100, similar to CPR device 100 discussed above. As such, similar components are not discussed with respect to FIG. 9. Rather than having an air intake and exhaust, as illustrated in FIG. 2, the electronic components of the CPR device 100 may be attached to a hot plate 902 or other device to absorb the heat from the components. FIG. 9 only illustrates the hot plate 902, but as will be understood by one skilled in the art, the electrical components of the central unit 103 would be coupled to the hot plate 902 in this example. To transfer the heat away from the electrical components, fluid may be pumped through tubing, conduit, or another type of transfer device to absorb the heat and move the heat away from the electrical components.

For example, the CPR device 100 illustrated in FIG. 9 includes tubing 900 which can surround the support legs 104 and/or the base member 105. In FIG. 9, the tubing 900 is shown surrounding both the base member 105 and the support legs 104. The tubing 900 may be continuous or may connect to or otherwise interact with a reservoir of fluid. Although not shown, a pump may be included to pump the fluid through the tubing. In such a configuration, the tubing may also act as a warming device for a patient. The pump, similar to the fans discussed above, may turn on and move fluid through the system when an internal temperature of the central unit 103 reaches a predetermined temperature.

In the example illustrated in FIG. 9, contaminated air and body fluids cannot enter any internal components of the CPR device 100 and the entirety of the CPR device can be cleaned to remove any potential pathogens before use on another patient.

Examples may operate on a particularly created hardware, on firmware, digital signal processors, or on a specially programmed general purpose computer including a processor operating according to programmed instructions. The terms "controller" or "processor" as used herein are intended to include microprocessors, microcomputers, ASICs, and dedicated hardware controllers. One or more aspects may be embodied in computer-usable data and computer-executable instructions, such as in one or more program modules, executed by one or more computers (including monitoring modules), or other devices. Generally, program modules include routines, programs, objects, components, data structures, etc. that perform particular tasks or implement particular abstract data types when executed by a processor in a computer or other device. The computer executable instructions may be stored on a non-transitory computer readable medium such as a hard disk, optical disk, removable storage media, solid state memory, RAM, etc. As will be appreciated by one of skill in the art, the functionality of the program modules may be combined or distributed as desired in various examples. In addition, the functionality may be embodied in whole or in part in firmware or hardware equivalents such as integrated circuits, field programmable gate arrays (FPGA), and the like. Particular data structures may be used to more effectively implement one or more aspects of the disclosed systems and methods, and such data structures are contemplated within the scope of computer executable instructions and computer-usable data described herein.

The previously described versions of the disclosed subject matter have many advantages that were either described or would be apparent to a person of ordinary skill. Even so, all of these advantages or features are not required in all versions of the disclosed apparatus, systems, or methods.

Additionally, this written description makes reference to particular features. It is to be understood that the disclosure in this specification includes all possible combinations of those particular features. For example, where a particular feature is disclosed in the context of a particular aspect or example, that feature can also be used, to the extent possible, in the context of other aspects and examples.

Also, when reference is made in this application to a method having two or more defined steps or operations, the defined steps or operations can be carried out in any order or simultaneously, unless the context excludes those possibilities.

Furthermore, the term "comprises" and its grammatical equivalents are used in this application to mean that other components, features, steps, processes, operations, etc. are optionally present. For example, an article "comprising" or "which comprises" components A, B, and C can contain only components A, B, and C, or it can contain components A, B, and C along with one or more other components.

Also, directions such as "vertical," "horizontal," "right," and "left" are used for convenience and in reference to the views provided in figures. But the [what] may have a number of orientations in actual use. Thus, a feature that is vertical, horizontal, to the right, or to the left in the figures may not have that same orientation or direction in actual use.

Although specific examples have been illustrated and described for purposes of illustration, it will be understood that various modifications may be made without departing from the spirit and scope of the disclosure. Accordingly, the invention should not be limited except as by the appended claims.

What is claimed is:

1. A mechanical cardiopulmonary resuscitation (CPR) device, comprising:
    a central unit having an internal chamber with one or more electronic components;
    a fan configured to intake air to the internal chamber;
    an exhaust configured to eject air from the internal chamber;
    an air deflector structured to direct air away from a head of a patient, wherein the air deflector is structured to tilt toward the lower body of the patient; and
    a disinfectant device configured to disinfect air in the internal chamber.

2. The mechanical CPR device of claim 1, wherein the air deflector is removable.

3. The mechanical CPR device of claim 1, wherein the air deflector includes an air intake path and an exhaust path.

4. The mechanical CPR device of claim 3, wherein each of the air intake path and the exhaust path are at least partially enclosed.

5. The mechanical CPR device of claim 3, wherein the air intake path and the exhaust path define an opening structured to receive a piston of the mechanical CPR device.

6. The mechanical CPR device of claim 1, wherein the air deflector includes a hose connected to the exhaust.

7. The mechanical CPR device of claim 6, wherein the hose is a first hose and the mechanical CPR device further includes a second hose connected to the fan.

8. The mechanical CPR device of claim 1, wherein the air deflector is "C" shaped.

9. The mechanical CPR device of claim 1, wherein the air deflector attaches to the central unit.

* * * * *